United States Patent [19]
Morejon

[11] Patent Number: 5,843,115
[45] Date of Patent: Dec. 1, 1998

[54] TROCAR INSERTION DEVICE

[76] Inventor: Orlando Morejon, 235 SW. 79th Ave., Miami, Fla. 33144

[21] Appl. No.: 738,844

[22] Filed: Oct. 28, 1996

[51] Int. Cl.$^6$ ..................................................... A61B 17/34
[52] U.S. Cl. ......................... 606/185; 606/167; 604/164; 604/264
[58] Field of Search .................................... 606/167, 170, 606/181, 182, 183, 184, 185; 604/164, 165, 170, 264

[56] References Cited

U.S. PATENT DOCUMENTS

| | | | |
|---|---|---|---|
| 5,314,417 | 5/1994 | Stephens et al. | 604/264 |
| 5,522,831 | 6/1996 | Sleister et al. | 606/182 |
| 5,538,509 | 7/1996 | Dunlap et al. | 604/264 |
| 5,620,456 | 4/1997 | Sauer et al. | 606/185 |

*Primary Examiner*—Michael Buiz
*Assistant Examiner*—David O. Reip
*Attorney, Agent, or Firm*—Malloy & Malloy,P.A.

[57] ABSTRACT

A trocar insertion device to facilitate the introduction of a conventional trocar into a patient, the insertion device including a generally elongate insertion arm that has a tubular configuration structured and disposed to removably receive a trocar mounted thereon, and a generally narrow and short guide segment extending from a forward end of the insertion arm. The guide segment includes a pointed tip structured and disposed to facilitate penetration of the guide segment through a patient's skin so as to define a small guide port in the patient's skin. Furthermore, a penetration resistance hub defined at the forward end of the insertion arm is provided and disposed to abut the patient's skin after initial penetration of the guide segment through the patient's skin, thereby resisting penetration of the insertion arm, and the trocar thereon, through the patient's skin until after a plurality of surgical blades protrude from the insertion arm to cut a corresponding number of incisions, extending from the guide port defined in the patient's skin, which define an entry opening wherethrough the insertion arm and the trocar disposed thereon penetrate the patient's skin, with minimal resistance and minimal skin trauma, to a desired depth.

32 Claims, 7 Drawing Sheets

TROCAR INSERTION DEVICE

BACKGROUND OF THE INVENTION

1. Field of Invention

The present invention relates to a trocar insertion device structured to be utilized with a variety of trocars so as to facilitate the initial introduction of the trocar into the patient in a safe and controlled manner which will provide minimal resistance to insertion, and accordingly minimal trauma to the patient's skin and a minimal risk of over insertion into the patient upon initial introduction.

2. Description of the Related Art

With the progression of modern medicine, many surgical procedures, which had traditionally been fully invasive, requiring complete exposure of a patient's internal organs at the site of the procedure, are being replaced by minimally invasive surgical procedures. These minimally invasive surgical procedures are commonly preferred due to their ability to achieve the same beneficial results as a fully invasive procedure, through small openings or ports formed in the patient.

Many of the more common types of minimally invasive surgical procedures require access to the abdominal region of a patient, and are generally termed laproscopic surgery procedures. Typically, these procedures involve the insufflation of a patient's abdominal region, thereby providing spacing between the external abdominal wall and the internal organs of the patient, and providing an adequate working environment. Specific access to that insufflated working environment is achieved by the formation of various ports through the patient's skin of the abdominal wall, and through which the surgical instruments will be introduced into the patient. In order to preserve maximum maneuverability within the patient and in order to maintain the integrity of the ports which are formed through the patient's skin, a series of instruments conventionally called trocars are first inserted through the patient's skin. The trocars function to rigidly define elongate passages or ports through which the elongate surgical instruments are inserted into the patient in order to perform the various procedures. Moreover, the trocars are often utilized and positioned throughout a patient so as to facilitate viewing of an operating region from different angles utilizing fiber optic cameras and the like. Accordingly, such procedures have proven increasingly safe and effective, and are becoming more and more common if they are an option.

A primary difficulty associated with such minimally invasive surgical procedures, however, involves the initial introduction of multiple trocars into the patient. In particular, in a conventional procedure multiple trocars, including a primary trocar as well as a number of secondary trocars, are generally utilized within the patient. While generally all of the trocars can function as ports for the introduction of a surgical instrument or for the viewing of the operating region, a major distinction between the primary trocar and the secondary trocars, is the fact that the primary trocar will be the first to be introduced into the body. It is the primary trocar that is often used to provide access to a fiber optic camera or other viewing means that permit some visual inspection of the interior abdominal region in order to help guide the positioning of the remaining secondary trocars. Specifically, it is preferred that the various secondary trocars be positioned at precise locations in accordance with the role the instruments extending therethrough will play during the surgical procedure. Of course, however, there are still substantial limitations to the effective viewing range through the single, primary trocar, and accordingly, the precise location for the introduction of some of the secondary trocars cannot be readily determined. Still, of primary concern is the introduction of the primary trocar, which must generally be done blindly with a doctor having to estimate the entry point of an appropriate location. As a result, because the doctor is unable to readily identify the specific internal organs which lie below a selected primary introduction site, the doctor must be exceedingly careful not to over insert the primary trocar and damage internal organs.

Although great care is generally taken with the introduction of the primary as well as the secondary trocars, the general nature and configuration of conventionally implemented trocars makes it quite difficult to provide truly safe and "controlled" introduction of the trocars. Specifically, most trocars are conventionally spiked tipped trocars which are inserted simply by puncturing the patient's skin. As a result, when introduction is necessary a point of introduction is selected and the trocar is merely pushed up against the patient's skin. At that point, considerable downward pressure is exerted by the doctor until the trocar punctures the patient's skin and proceeds into the abdominal region. In fact, such introduction is often accompanied by a loud popping sound as a result of the force necessary to actually puncture the patient's skin into an insufflated abdomen.

Of the conventional spiked trocars, some are equipped with intricately formed, pointed tips, and some are utilized with introducing spikes. Generally, those with some form of introduction assistance spike include an elongate pointed element that extends through an axis of the trocar such that its spiked tip protrudes through the open end of the trocar. As a result, subsequent to penetration of the trocar into the patient, the axially disposed element is removed from the trocar leaving only the trocar to define an accessible port into the patient.

In an attempt to at least partially increase the safety of these crude trocar introduction methods, the manufacturers of some conventional spiked trocars have turned to the development of safety shields or like means to at least partially shield and protect a patient's internal organs from the pointed trocar tip. Unfortunately, however, such shields do not generally function until after the trocar has penetrated the patient's skin. As such, given the crude, brute force methods of introduction that are utilized, positioning of the shield is often too late if the trocar has been over inserted at or near various internal organs. As a result, there is still substantial need in the art for a means to introduce a trocar into a patient in a truly safe and controlled fashion.

In particular, through the use of the present invention it is seen that the primary variables associated with ensuring controlled entry of a trocar into a patient include good visibility, reduced force to penetrate the tissues by the trocar, and an experienced surgeon. Still, however, even the most experienced surgeon cannot fully overcome the deficiencies of conventional trocars with regard to the other variables. Furthermore, even in circumstances where appropriate introduction of the trocar is achieved utilizing the conventional methods, substantial skin trauma results as the patient's skin is effectively ripped apart to create the puncture. Such brute strength introduction can not only result in substantial skin trauma, but it can also make it substantially difficult to effectively reseal the opening, after the procedure is completed, in a manner which will leave minimal scarring and which will heal relatively quickly. Accordingly, there is a substantial need in the art for an improved trocar insertion device which is substantially safe to utilize, can provide for substantially facilitated introduction into the patient with minimal resistance, thereby minimizing the chances of over insertion and excessive skin trauma, and which is capable of providing a doctor with some clear, visible indications that a selected insertion location is a safe and appropriate site, even when it is the primary trocar that is being introduced. Moreover, such a device should be ideally be included as part of a single, easy to operate and manipulate self-contained unit, which is usable with most conventional trocars and does not require extensive training or procedures to implement.

SUMMARY OF THE INVENTION

The present invention is directed towards a trocar insertion device to be utilized to facilitate the introduction of a trocar into a patient. The insertion device includes initially a generally elongate insertion arm. The insertion arm, which includes a forward end and a rear end, has a generally tubular configuration, and is structured and disposed to removably receive the trocar, which will be inserted into the patient, removably disposed thereon.

Further, the trocar insertion device includes a guide segment. The guide segment is structured to extend from the forward end of the insertion arm. Moreover, the guide segment includes a pointed tip structured and disposed to facilitate penetration thereof through a patient's skin so as to define a guide port in the patient's skin. Preferably, the guide segment is substantially narrow, thereby minimizing a size of the guide port to be made and minimizing a resistance against its penetration exhibited by the patient's skin during its initial introduction.

Disposed between the guide segment and the insertion arm is a penetration resistance hub. The penetration resistance hub is structured and disposed to abut a patient's skin upon initial penetration of the guide segment through the patient's skin. As such, the penetration resistance hub will resist penetration of the insertion arm, and the trocar disposed thereon, as the doctor pushes down with minimal force to achieve the initial, limited penetration of only the guide segment.

Once the guide port has been defined by the guide segment, in order to provide for the facilitated introduction of the insertion arm, as well as the trocar disposed thereon, through the patient's skin, the trocar insertion device further includes retractable cutting means. Specifically, the retractable cutting means are structured to safely and precisely cut at least one incision, extending from the guide port previously defined in the patient's skin by the guide segment. As a result, the retractable cutting means will define a larger entry opening where through the insertion arm, and the trocar, can pass in a slow and controlled manner, with minimal resistance and with minimal skin trauma, into a desired depth within the patient.

It is an object of the present invention to provide a trocar insertion device which provides for controlled initial introduction of a trocar into a patient so as to minimize a risk of over insertion and/or damage to internal organs at the site of insertion.

A further object of the present invention is to provide a trocar insertion device which facilitates the introduction of a trocar into a patient with minimal skin trauma in order to provide for improved healing of a patient at the site of the entry opening.

Also an object of the present invention is to provide a trocar insertion device which requires minimal insertion pressure being exerted in order to provide for complete and effective introduction of a trocar in a safe and very controlled manner.

Another object of the present invention is to provide an improved trocar insertion device which can be utilized with a variety of conventional trocars in a safe, efficient, and highly effective manner.

Yet another object of the present invention is to provide for a trocar insertion device which provides for the actual introduction of the trocar into the patient without any exposed sharp or pointed surfaces, thereby minimizing a risk of inadvertent damage to internal organs.

A further object of the present invention is to provide a trocar insertion device which is convenient to handle and manipulate during introduction of the trocar.

An additional object of the present invention is to provide a trocar insertion device which is capable of achieving facilitated and controlled introduction of a trocar into a patient, but which also provides for an effective, sealing engagement to remain between the trocar and the patient's skin.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Shown throughout the Figures, the present invention is directed towards a trocar insertion device, generally indicated as 10. In particular, the trocar insertion device 10 is structured to receive and facilitate the introduction of a trocar 80 into a patient for the performance of various minimally invasive surgical procedures. Moreover, the trocar insertion device 10 of the present invention introduces the trocar 80 through the patient's skin 90 in such a manner that the introduction is substantially safe and controlled at all times during insertion, thereby significantly minimizing the risk of excessive skin trauma or damage to internal organs located at the site of introduction. The trocar 80 itself may include any of a variety of conventional trocar configurations, and may alternatively include a trocar configuration including a distal inflatable cuff 82 into which air is introduced through an inflation port 84 disposed at a head of the trocar 80.

Looking to the preferred embodiments of the trocar insertion device 10, as illustrated in the Figures, it includes a generally elongate insertion arm 20. The insertion arm 20, which includes a forward end 22 and a rear end 24, includes a generally tubular configuration so as to receive the trocar 80 removably disposed thereon. In particular, the trocar 80 is structured to slide over a length of the insertion arm 20, which is preferably only slightly narrower than an axial passage of the trocar 80, in order to provide for corresponding introduction with the insertion arm 20 through the patient's skin 90.

Extending, preferably concentrically, from the forward end 22 of the insertion arm 20 is a guide segment 30. The guide segment 30, which includes a pointed tip 34, is structured and disposed to substantially easily penetrate through the patient's skin 90 in a controlled manner in order to define a guide port 92 in the patient's skin. Specifically, the guide segment 30 will preferably be substantially narrow in diameter, approximating the size of a larger needle or like item which is capable of piercing the patient's skin 90 in a generally facilitated, and minimally resisted manner. Moreover, the guide segment 30 is also preferably substantially short, thereby minimizing a penetration distance thereof through the patient's skin and protecting against accidental injury to insertion of internal organs at the insertion site. In particular, it is seen that a primary function of the guide segment 30 is to define the guide port 92 and provide a safe, effective anchorage to the guide port 92 for subsequent insertion of the trocar 80. As such, only a length and diameter sufficient to easily penetrate through the skin and achieve that purpose is required and the guide segment can be relatively small. Specifically, in the preferred embodiment of the present invention, the diameter of the guide segment 30 will preferably be in a range of about 2 mm to 4 mm, and the overall length of the guide segment 30 will preferably be within a range of approximately 10 mm to 20 mm. Nevertheless, it should be understood that dimensions outside of that range may also be utilized in certain circumstances, so long as those dimensions are consistent with the requirement that initial penetration through the patient's skin 90 be facilitated, with minimal risk of over insertion.

Figure 2:
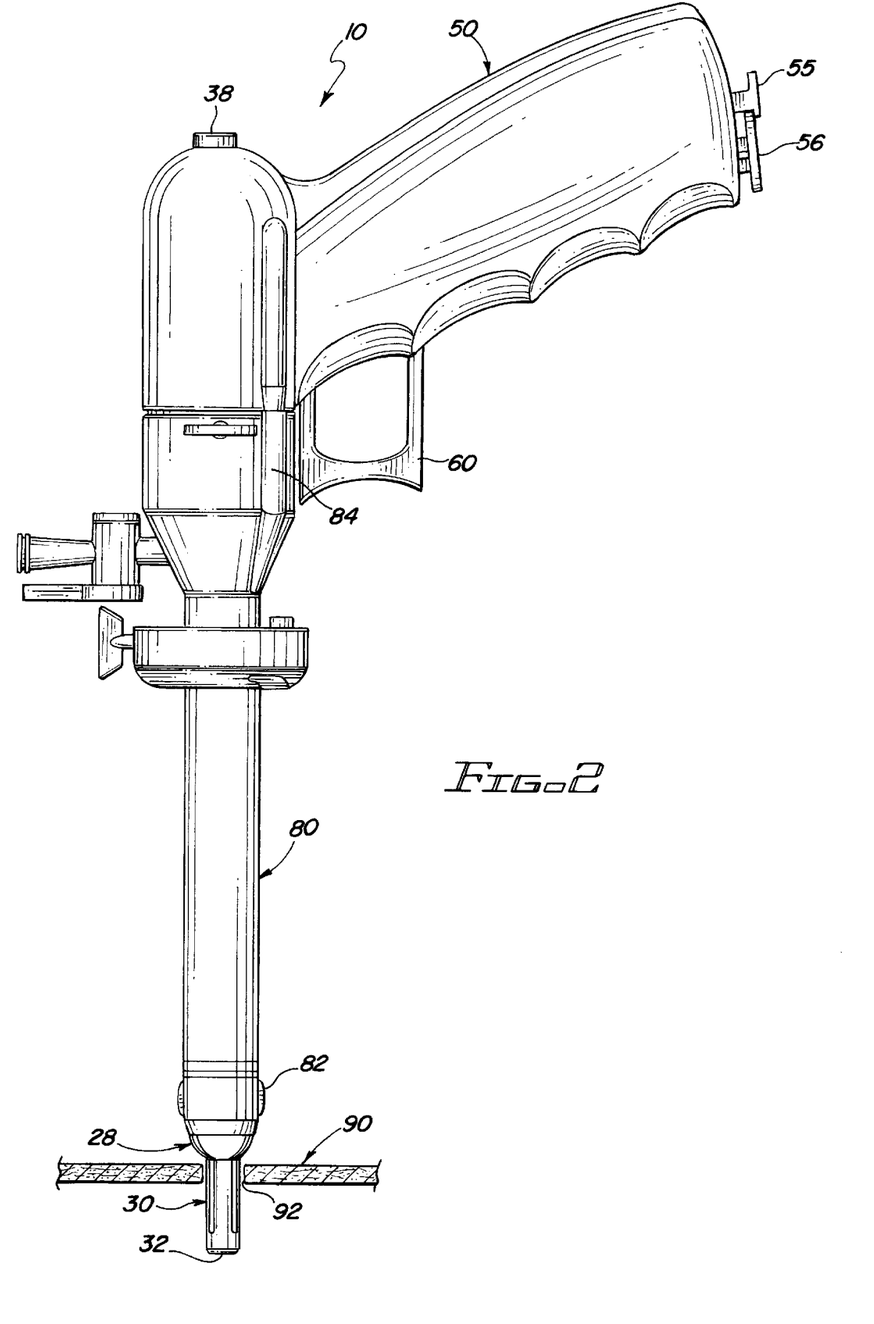
FIG. 2 is a side view of the trocar insertion device of the present invention with a trocar disposed thereon, and positioned in an intermediate stage of insertion subsequent to the initial penetration of the guide segment through the patient's skin.

In order to further ensure that over insertion of the guide segment 30 is not achieved upon its initial penetration through the patient's skin 90, and more particularly to ensure that the insertion arm 20 does not immediately follow the guide segment 30 through the patient's skin, the trocar insertion device 10 of the present invention further includes a penetration resistance hub 28. The penetration resistance hub 28 is disposed between the guide segment 30 and the insertion arm 20 in order to abut the patient's skin 90, once the guide segment has sufficiently, and preferably completely, penetrated through the patient's skin, and thereby resist penetration of the insertion arm 20, and the trocar 80 disposed thereon, through the patient's skin 90 upon that initial penetration of the guide segment 30 into the patient's skin 90. In the preferred embodiments, the penetration resistance hub 28 is defined at the forward end 22 of the insertion arm 20. Specifically, the guide segment 30 is preferably structured to be generally narrower than the forward end 22 of the insertion arm 20, thereby defining the penetration resistance hub 28. From this it can be seen, that subsequent to introduction of the guide segment 30 through the patient's skin 90, the penetration resistance hub 28, as illustrated in FIG. 2, will provide a sharp, blunt surface that resists continued penetration through the small guide port 92 formed by the guide segment 30. To aid in this function, it is also preferred that the penetration resistance hub 28 extend away from the guide segment 30 at an angle of substantially near 90 degrees, tapering as desired thereafter. Although the integral penetration resistance hub 28 is preferred, it should be noted that in alternative embodiments, the penetration resistance hub may include a separate inflatable cuff or retractable or removable collar disposed at the forward end 22 of the insertion arm 20 in order to prevent the continued penetration of the insertion arm 20 into the guide port 92 subsequent to initial penetration of the guide segment 30.

Looking with more particularity to the guide segment 30, and the pointed tip 34 thereof, it may include a variety of configurations so long as it provides a sufficiently sharp point to facilitate passage through the patient's skin. For example, in an alternative, less preferred embodiment, the pointed tip 34 may be integrally formed at the end of the guide segment 30. However, in order to improve the overall safety of the trocar insertion device 10, especially upon subsequent introduction of the insertion arm 20 and the trocar 80 through the patient's skin 90, it is preferred that the pointed tip 34 be retractable and/or otherwise removable. Specifically, in the preferred embodiments, subsequent to the initial penetration of the guide segment 30 through the patient's skin 90 to form the guide port 92, the pointed tip 34 is concealed leaving only a generally blunt end of the guide segment 30 which leads the way during subsequent introduction of the insertion arm 20 and trocar 80. Along these lines, it should be noted that the guide segment 30 in its entirety may also be configured to be retractable or removable, however, it is preferred that a body of the guide segment 30 remain in an extended position in order to maintain anchorage and facilitate guided, properly aligned introduction of the insertion arm 20 and trocar 80 over the guide port 92 during the subsequent phases of the trocar insertion. As such, a majority of the guide segment 30, including its body, may be integrally formed with the insertion arm 20, with the exception of at least the preferred, retractable or removable, pointed tip 34.

Figures 1, 4:
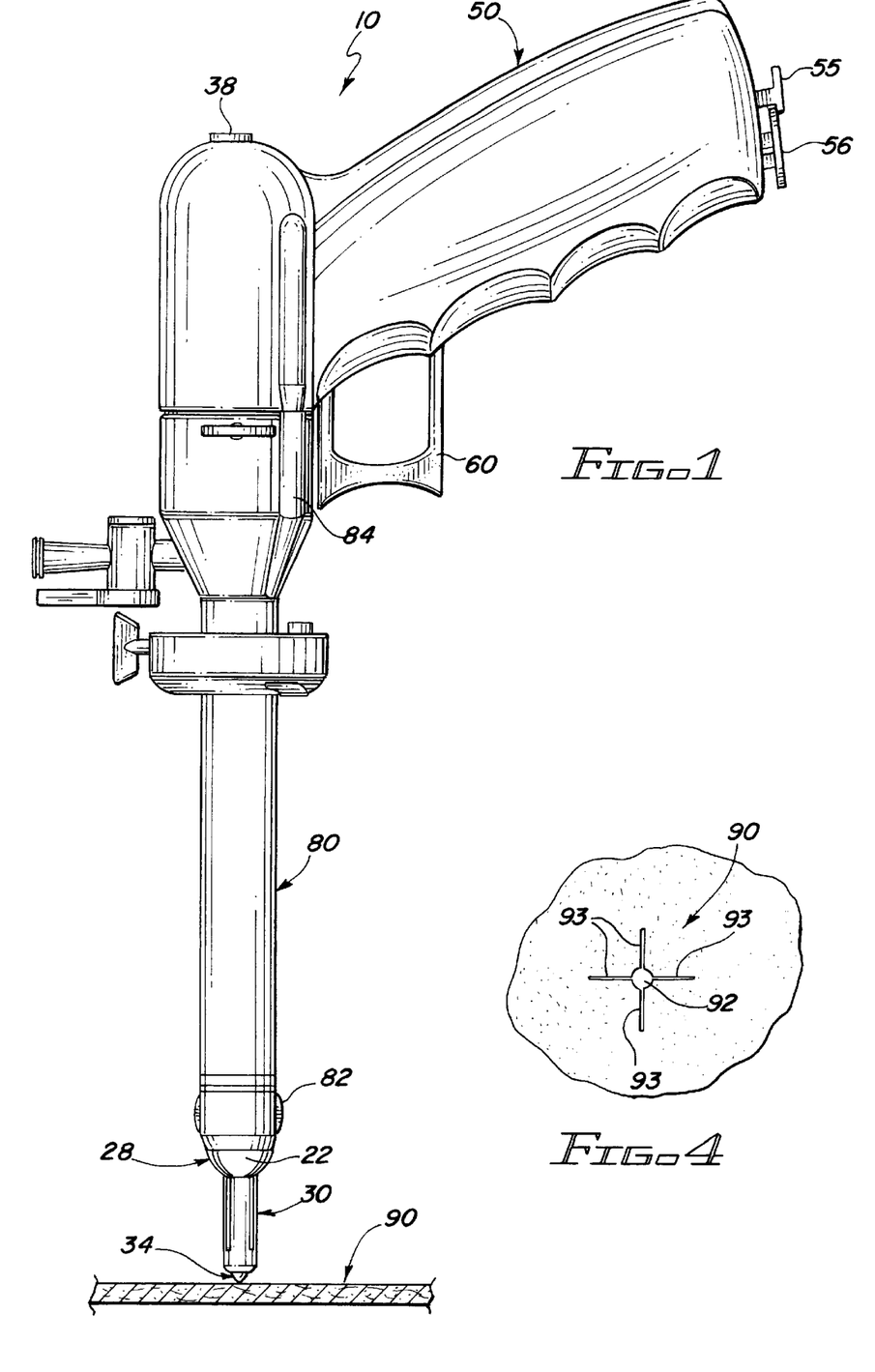
FIG. 1 is a side view of the trocar insertion device of the present invention with a trocar positioned thereon, and in position to begin insertion into a patient's skin.
FIG. 4 is a top plan view of the patient's skin at the site of insertion illustrating the configuration of the guide port and entry opening defined by the preferred embodiment of the trocar insertion device of the present invention.
Figures 5, 10, 11, 14:
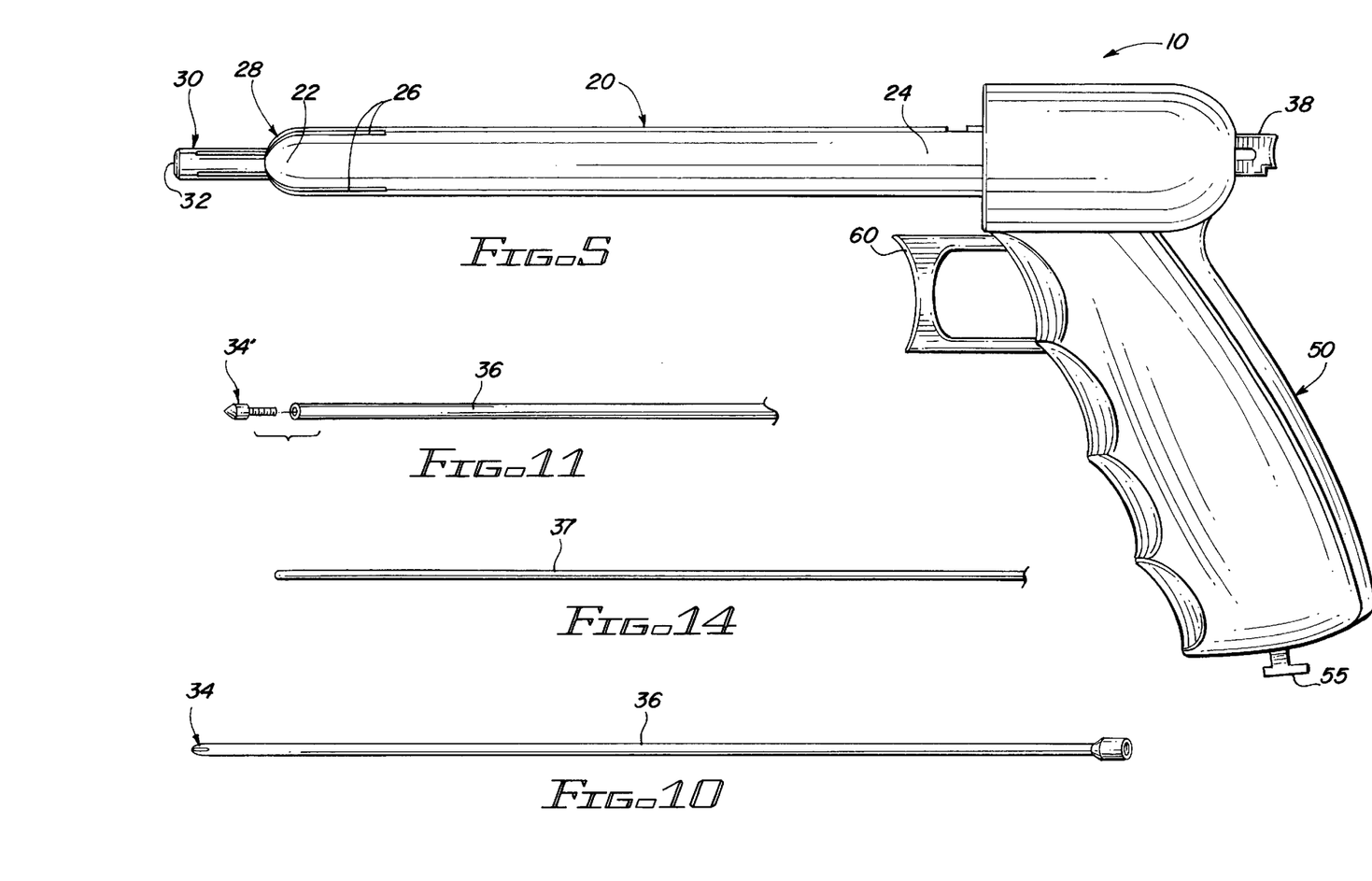
FIG. 5 is a side view of the trocar insertion device of the present invention.
FIG. 10 is a side view of a first embodiment of the pointed tip of the guide segment of the present invention.
FIG. 11 is a partial, side view of an alternative embodiment of the pointed tip of the guide segment of the present invention.
FIG. 14 is a side view of the viewing means and/or insufflation means of an alternative embodiment of the trocar insertion device of the present invention.
Figure 6:
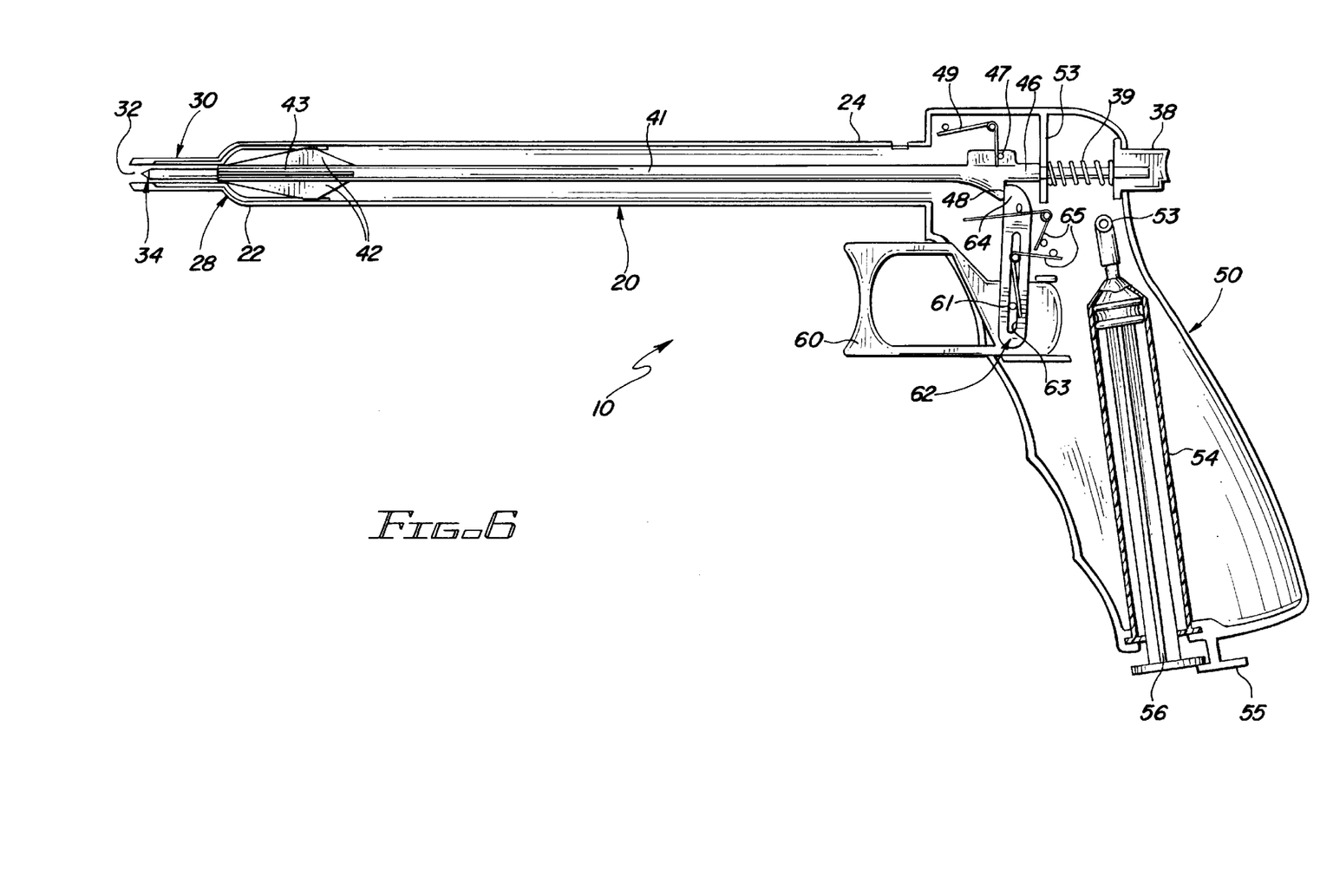
FIG. 6 is a side cross-sectional view of a preferred embodiment of the trocar insertion device of the present invention.

Looking to FIGS. 6, 10, and 11, although the pointed tip 34 may be substantially small so as to retract only slightly into the guide segment 30 until it is concealed, in the preferred embodiment, the pointed tip 34 is disposed at a distal end of an elongate extension rod 36. In this embodiment, the pointed tip 34 can be integrally formed with the extension rod 36, or as illustrated in FIG. 11, may be structured to be removably secured to the extension rod 36, thereby providing some replacability and/or independent sterilization of the pointed tip 34'. Furthermore, in this embodiment the pointed tip 34 and extension rod 36 are structured to extend through a length of the insertion arm 20 such that preferably only the pointed tip 34 extends through an open end 32 of the body of the guide segment 30, as illustrated in FIG. 1.

The pointed tip 34 is preferably independently retractable subsequent to initial penetration of the guide segment 30 into the patient, and is preferably configured to remain in a normally concealed orientation unless protrusion through the open end 32 of the guide segment 30 is specifically desired. To achieve this, the extension rod 36 is preferably connected with an actuation button 38, which is externally actuatable in order to provide for selected protrusion of the pointed tip 34 through the open end 32 of the guide segment 30. In this embodiment, a biasing spring 39 is connected with the extension rod 36 and abuts an internal stopper element 53 so as to normally bias the extension rod 36, and therefore the pointed tip 34, into the concealed orientation. As such, upon initial penetration of the guide segment 30 through the patient's skin 90, a user of this embodiment must merely push on the actuation button 38, exposing the pointed tip 34 through the open end 32 of the guide segment 30 during initial penetration through the patient's skin 90 to define the guide port 92. Once this initial penetration of the guide segment 30 has been achieved, the actuation button 38 is merely released and the biasing spring 39 returns the pointed tip 34 to a retracted, normally concealed orientation. In this regard, it should be understood that a variety of assemblies may be incorporated so as to provide for this preferred retractability of the pointed tip 34.

In addition to being retractable, in a preferred embodiment, the pointed tip 34, and the preferred extension rod 36 to which it is secured, are not only retractable, but are also completely removable. In such an embodiment, upon removal of the extension rod 36 and pointed tip 34, an axial passage remains through which viewing means or insufflation means, illustrated generally in FIG. 14 as 37, may pass. In particular, the viewing means, which may include any conventional viewing means such as fiber optic camera, will generally include a tubular segment 37 which can extend through the extension arm 20 and out through the open end 32 of the guide segment 30 in order to provide a doctor with an appropriate view of the general vicinity of insertion, prior to substantial penetration of the trocar insertion device 10 and the trocar 80 itself. As such, if the insertion site initially selected is deemed to be inappropriate or possibly hazardous, the trocar insertion device 10 may be easily removed leaving only a small guide port 92. In many circumstances, however, the trocar insertion device 10 may merely be manipulated so as to be aimed away from nearby internal organs during subsequent introduction of the insertion arm 20 and trocar 80. Similarly, the trocar insertion device 10 may be utilized for the initial insufflation of the patient's abdomen. In particular, insufflation means such as an elongate tube 37 may extend through the insertion arm 20 and out through the open end 32 of the guide segment 30 in order to provide for the introduction of the appropriate insufflation gas into the patient. Still, however, it should be noted that a separate tube may not be necessary for the insufflation means if the axial channel which remains through the insertion arm 20 and guide segment 30, upon removal of the extension rod 36 and pointed tip 34 of the guide segment 30, is sufficiently integral so as to used as part of the insufflation means. Furthermore, in yet another alternative embodiment, it is also seen that the viewing means and/or insufflation means may be permanently and integrally formed as part of the trocar insertion device 10, and essentially extend through the walls of the guide segment 30 to provide for effective functioning whether or not the pointed tip 34 is removed.

The trocar insertion device 10 of the present invention further includes retractable cutting means, generally 40. The retractable cutting means 40 are structured to cut at least one incision 93 extending from the guide port 92 defined in the patient's skin 90 by the guide segment 30. The at least one incision 93 formed by the retractable cutting means defines an entry opening where through the insertion arm 20 and trocar 80 disposed thereon may subsequently penetrate the patient's skin with minimal resistance and minimal skin trauma, to a desired depth.

Specifically, the retractable cutting means 40 includes at least one, but preferably three or four surgical blades 42. Further, each surgical blade 42 is preferably outwardly tapered, away from the guide segment 30, as illustrated in the Figures. As such, the surgical blades 42 are preferably configured to cut outwardly from the guide port 92 in order to form the incisions 93 that define the entry opening. In particular, whether cutting away from the guide port 92, as in the preferred embodiment, or cutting towards the guide port 92, the incisions 93 formed by the surgical blades 42 of the retractable cutting means 40 function to define a plurality of individual flaps which can easily, and in a minimally traumatic fashion fold back to fully define the entry opening through which the insertion arm 20 and the trocar 80 disposed thereon may easily penetrate the patient's skin 90. In this regard, some stretching of the patient's skin around a perimeter of the trocar 80 will result, thereby providing a secure seal between the patient's skin 90 and the trocar 80. Still, so as to provide for minimal stretching of the patient's skin and more facilitated retraction thereof, three or four of the surgical blades 42 are preferably included to form three or four incisions 93 at appropriate spaced orientations about the guide port 92. Furthermore, so as to facilitate uniform cutting of the incisions 93, each of the surgical blades 92 are preferably secured with one another, and in fact are preferably integrally formed with one another and extend from a central blade housing 43.

As illustrated in the Figures, the retractable cutting means 40 are structured to withdraw, preferably into the insertion arm 20, such that during initial penetration of the guide segment 30 into the patient's skin 90, the retractable cutting means 40 are completely concealed and will not cut into the patient's skin 90. After that initial penetration of the guide segment 30 into the patient's skin 90 so as to define a guide port 92, however, the retractable cutting means 40 are configured to extend, preferably from the forward end 22 of the insertion arm 20, into the guide port 92 in order to form the plurality of incisions 93. In the preferred embodiment, the surgical blades 42 of the retractable cutting means 40 are structured to retractably protrude through at least one, but preferably a plurality, corresponding the number of surgical blades 42, of slits 26 formed at the forward end 22 of the insertion arm 20. Moreover, the slits 26 preferably extend into the hollow tubular configuration of the guide segment 30. As such, it is seen that the surgical blades 42 essentially emerge from within the guide port 90, due to the tapered configuration of the surgical blades 42 and the presence of the guide segment 30 within the guide port 92, such that as the surgical blades 42 are pushed further towards the open end 32 of the guide segment 30, the expanding tapered configuration increases the size of the incisions 93 to almost a perimeter of the insertion arm 20. Therefore, subsequent introduction of the insertion arm 20 and the trocar 80 are facilitated, preferably subsequent to retraction of the surgical blades 42 into a normally retracted orientation within the insertion arm 20.

Figures 3, 12:
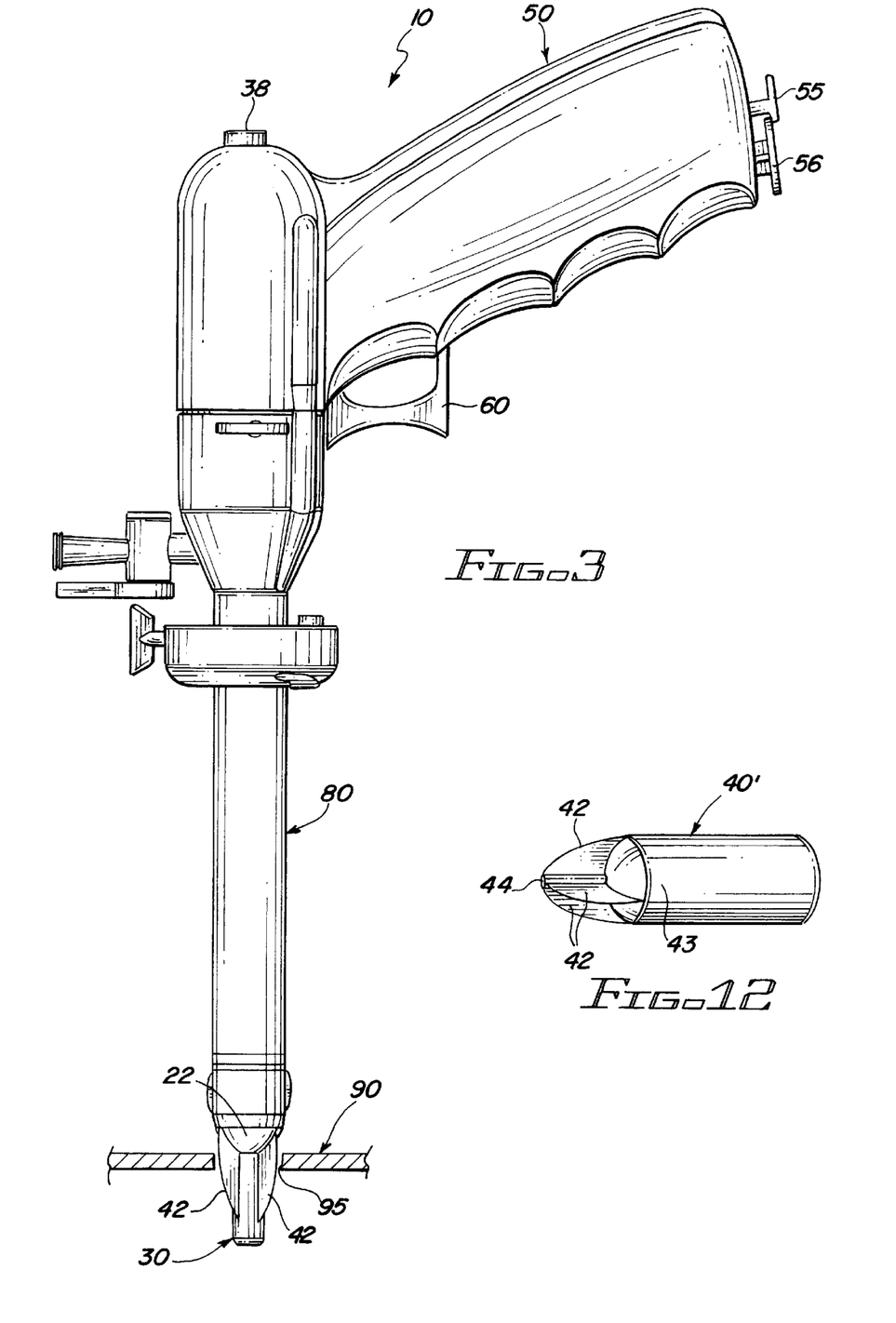
FIG. 3 is a side view of the trocar insertion device of the present invention with a trocar disposed thereon, and illustrating a later stage of insertion wherein the retractable cutting means define the entry openings through which the trocar and insertion arm of the trocar insertion device will be inserted into the patient.
FIG. 12 is a side view of an alternative embodiment of the retractable cutting means of the present invention.
Figure 13:
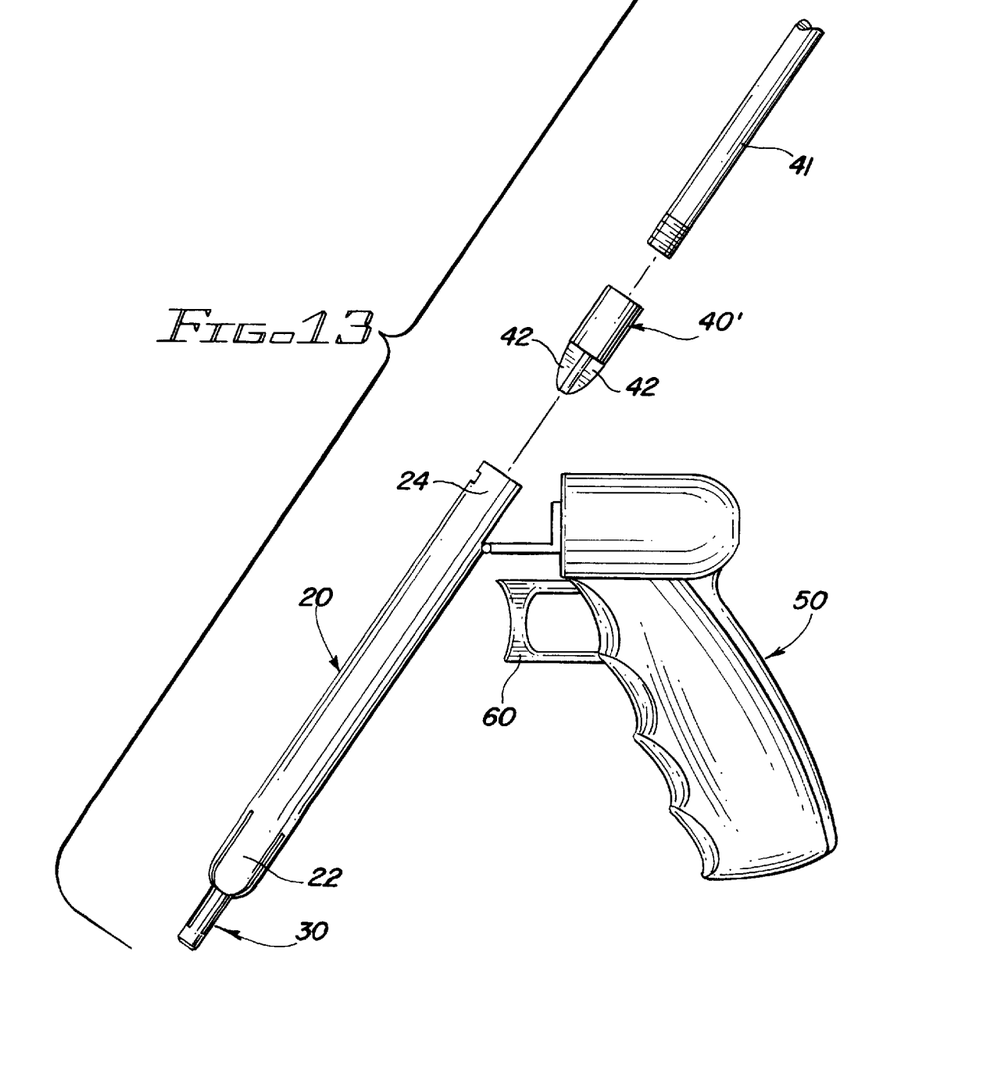
FIG. 13 is a side view of an alternative embodiment of the trocar insertion device of the present invention, including the removable embodiment of the retractable cutting means of FIG. 12.

Looking further to the preferred embodiment of the retractable cutting means 40, it preferably includes an elongate extension segment 41 which extends through the insertion arm 20, and preferably terminates at the central blade housing 43 from which the surgical blades 42 extend. In this regard, although the elongate extension segment 41 and the central blade housing 43 may be integrally formed with one another, it is also seen that in an alternative embodiment of the retractable cutting means 40', as illustrated in FIGS. 12 and 13, the central blade housing 43 may be structured to be removably secured with the elongate extension segment 41, thereby facilitating replacement of the surgical blades 42 and/or the entire central blade housing 43 during subsequent procedures. Such removability therefore significantly improves the safe, sterile reusability of the trocar insertion device 10 of the present invention. In this regard, and as illustrated in FIG. 13, the insertion arm 20 may be structured to pivot from a normal operative orientation to provide for the facilitated removal and reintroduction of the retractable cutting means 40 therein.

Extending from the rear end 24 of the insertion arm 20, are the handle means 50. The handle means 50 are structured to be easily and conveniently grasped by a user in order to facilitate the controlled, selective introduction of the guide segment 30, the retractable cutting means 40, and the trocar 80 through the patient's skin in various, desired stages. Further, as illustrated in the preferred embodiment of the Figures, the handle means 50 will preferably include a contoured, gun handle type configuration in order to facilitate effective actuation of various components of the trocar insertion device 10, as needed, and so as to enable adequate amounts of leverage to be maintained by the user during insertion of various portions of the trocar insertion device 10 through the patient's skin.

The handle means 50, which preferably contain the previously recited internal stopper element 53, are further structured and disposed to contain and appropriately position trigger means. The trigger means are connected with the retractable cutting means 40 in order to direct controlled movement of the retractable cutting means 40, from its preferred, normally retracted orientation, through the patient's skin as previously recited. Preferably, the trigger means are structured to normally bias and therefore maintain the retractable cutting means 40 concealed and shielded in a retracted orientation, preferably within the insertion arm 20. Moreover, the trigger means are preferably structured to automatically retract the retractable cutting means 40 into their retracted orientation immediately upon their release or upon the retractable cutting means 40 protruding a maximum, safe, cutting distance, thereby substantially ensuring that the retractable cutting means 40 are not over inserted into the patient's skin 90 and are not exposed during subsequent insertion of the insertion arm 20 and trocar 80 into the patient. In the preferred embodiment illustrated in FIG. 6, the elongate extension segment 41 of the retractable means 40 is connected with biasing means 49 structured and disposed to normally urge the elongate extension segment 41, and therefore the entire retractable cutting means 40, away from the forward end 22 of the insertion arm 20 in order to normally maintain the surgical blades 42 of the retractable cutting means 40 concealed and shielded in the retractable orientation. Moreover, in this embodiment the biasing means 49 includes a biasing element which engages a pin or like protrusion 47 disposed at a rear end 46 of the elongate extension segment 41, such that its biasing force may be overcome in order to permit cutting protrusion of the surgical blades 42, however, upon release of affirmative outward, pushing engagement thereof, will automatically push the retractable cutting means back into its normal, retracted orientation. In order to gradually, and in a controlled fashion direct the retractable cutting means 40 out of the retractable orientation for controlled introduction of the surgical blades 42 into the patient's skin 90, the trigger means of the preferred embodiment further include an externally actuatable hammer element 62. The externally actuatable hammer element 62 is structured to engage and therefore push the retractable cutting means 40 out of the retractable orientation and into a cutting orientation. Looking specifically to FIG. 6, the externally actuatable hammer element 62 of the preferred embodiment includes an elongate slot 63 formed therein. The slot 63 is structured to receive a pin 61, connected to an external trigger 60, therethrough. As such, when the external trigger 60 is pushed inwardly, the pin 61 rides through the elongate slot 63, pivoting the hammer element 62. Accordingly, a head 64 of the hammer element 62, which engages an abutment segment 48 at the rear end 46 of the retractable cutting means 40 pushes the retractable cutting means 40 into the cutting orientation in accordance with the pivotal movement thereof. In this regard, when the external trigger 60 is released, the biasing means 49 returns the retractable cutting means 40 into its retracted orientation. Moreover, after the externally actuatable hammer element 62 has pivoted sufficiently to protrude the cutting blades 42 of the retractable cutting means 40 to their maximum, safe, cutting distance, it is seen that the hammer element 62 will disengage the retractable cutting means 40 and thereby permit the biasing means 49 connected with the retractable cutting means 40 to immediately push the retractable cutting means 40 back into their retracted orientation. Additionally, a further biasing element 65 may be further included to reset the trigger 60 and the hammer element 62 subsequent to their release.

Figures 7, 8:
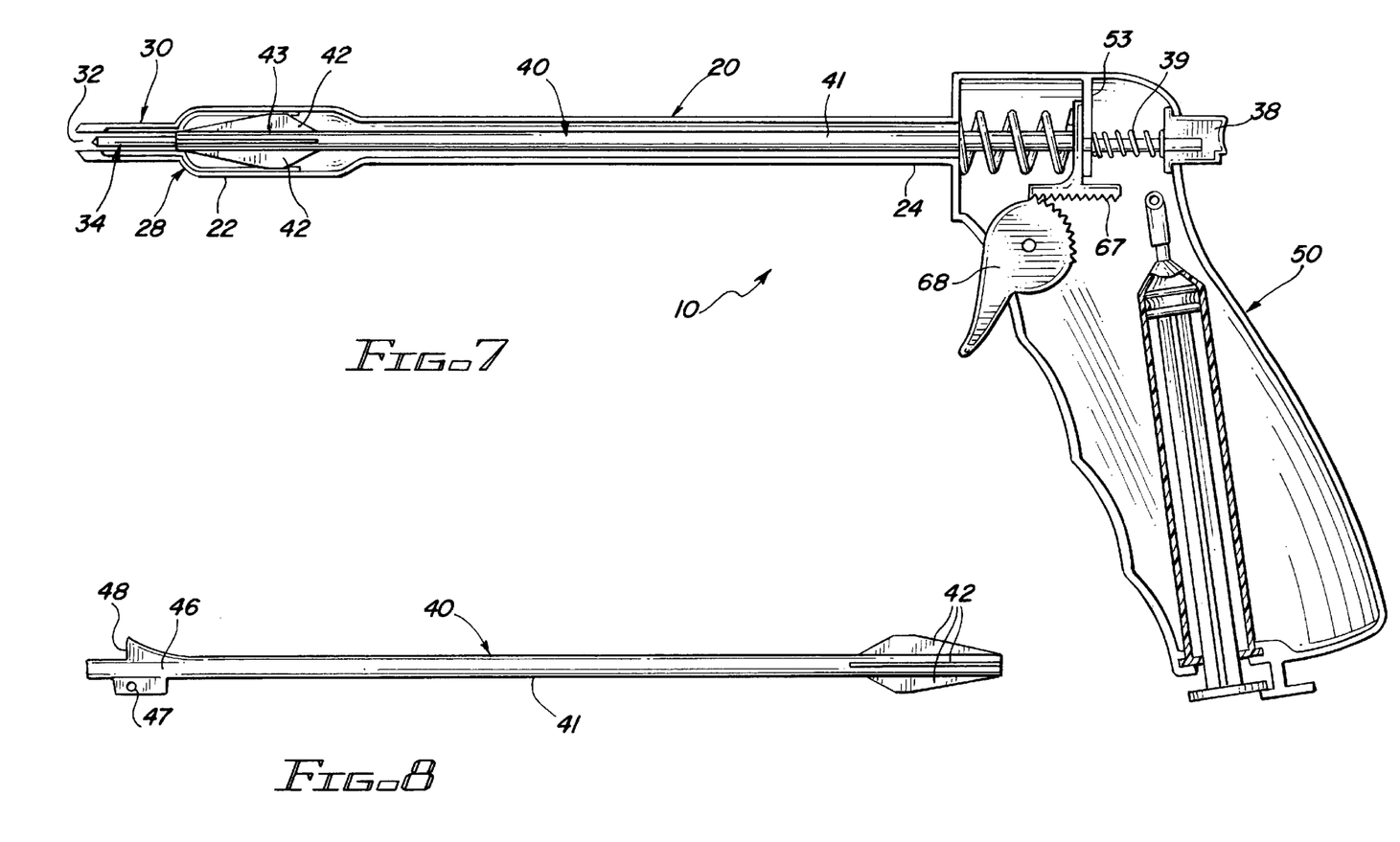
FIG. 7 is a side cross-sectional view of an alternative embodiment of the trocar insertion device of the present invention.
FIG. 8 is a side view of the preferred retractable cutting means of the present invention.
Figure 9:
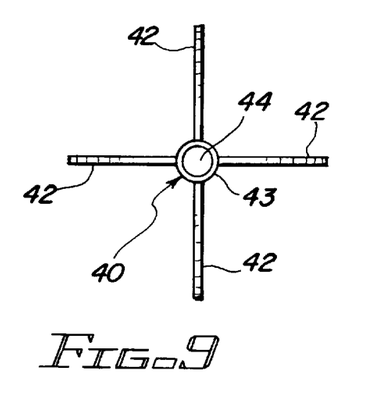
FIG. 9 is an end view of the preferred embodiment of the retractable cutting means of the present invention.

While the embodiment of FIG. 6 illustrates a preferred trigger means, in an alternative embodiment of FIG. 7, the biasing means may include a spring 69 which is connected at the rear end 46 of the extension segment 41 of the retractable cutting means 40 and must be expanded to permit movement of the retractable cutting means 40. Specifically, the spring 69 is structured to resist movement of the retractable cutting means 40 into the cutting orientation, and thereby urge the retractable cutting means back into the retracted orientation when they are not affirmatively being pushed into the cutting orientation by the user. In this embodiment, a gear-type trigger 68 is incorporated, including a plurality of gear teeth thereon. The gear trigger 68 is structured to engage a plurality of gear teeth on an interior track 67 connected at the rear end 46 of the retractable cutting means 40. As such, as the gear trigger 68 is actuated, the gear teeth ride engage one another, pushing the retractable cutting means 40 into the cutting orientation. In this embodiment, as well as in the previous embodiment, once the trigger 60 or 68 is released, the retractable cutting means normally return to the retracted orientation. If, however, the trigger 60 or 68 is not released and the retractable cutting means reach the maximum, safe, cutting distance, the length of travel of the gear teeth will be exhausted and engagement therebetween will be released to permit automatic retraction of the retractable cutting means 40.

As previously recited, the pointed tip 34 of the guide segment 30 is preferably retractable and is preferably connected at a distal end of an extension rod 36. In the preferred embodiments of the present invention, in order to facilitate independent movement and retraction of the pointed tip 34, independent from the retractable cutting means 40, while also maintaining appropriate axial positioning of the pointed tip 34, the retractable cutting means 40 will preferably include an axial opening 44 where through the extension rod 36 and pointed tip 34 extend into the guide segment 30. As such, the pointed tip 34 will be able to retract and be removable independent from the retractable cutting means 40.

Looking specifically to FIGS. 1, 2 and 3, when insertion of the trocar insertion device 10 and trocar 80 of the present invention is desired, a user grasping the handle 50 will utilize their thumb to push the actuation button 38 and expose the pointed tip 34 of the guide segment 30. At that point, utilizing the preferred embodiment, the generally narrow, easy to introduce guide segment 30 is pushed through the patient's skin 90 to form a guide port 92 as illustrated in FIG. 2. Subsequently, the actuation button 38 is released and the pointed tip 34 retracts into the hollow, tubular configuration of the guide segment 30, after which it may remain retracted during subsequent stages or can be completely removed, leaving only the axial opening 44. Next, the user, applying only small amounts of downward pressure, begins to pull on the trigger 60, gradually exposing the cutting blades 42 of the retractable cutting means 40 until the plurality of incisions 93 are formed, as illustrated in FIG. 3. Once the incisions 93 are fully formed, the trigger 60 is released so that the retractable cutting means 40 automatically retract into a concealed, retracted orientation within the insertion arm 20. At that point, with minimal downward pressure the insertion arm 20 and trocar 80 disposed thereon are pushed through the entry opening that is fully defined as the flaps of skin between the incisions 93 fold back. The trocar insertion device 10 can then be removed from the trocar 80, leaving only the trocar 80 in proper position within the patient. Furthermore, when the trocar 80 is removed, the minimally traumatic introduction facilitates suturing of the incisions 93 for substantially improved healing.

As previously recited, the trocar insertion device 10 of the present invention may be utilized with any conventional type trocar 80. When, however, the trocar insertion device 10 is utilized with a trocar 80, as illustrated in FIGS. 1–3, which incorporates an inflatable cuff 82, means to facilitate the inflation of that inflatable cuff 82 may also be provided. In this embodiment, a channel 54 into which a syringe 56 may be introduced is included within the handle 50. As such, the handle 50 receives the syringe 56, which can be clipped in place by an actuatable clip 55, for internal connection with an internal fluid flow valve 53. The internal fluid flow valve 53 is structured to receive the air pushed from the syringe 56 and pass it down into the inflation port 84 in the head of the trocar 80 for inflation of the inflatable bladder 82.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. For example, the term skin has been utilized in the illustration of the function of the present invention and should not be taken in a limiting sense, but rather should include the outermost epidermal layers and/or various internal tissue layers which must generally be penetrated during minimally invasive surgical procedures.

Now that the invention has been described,

What is claimed is:

1. A trocar insertion device comprising:
- a generally elongate insertion arm, said insertion arm including a forward end and a rear end,
- said insertion arm including a tubular configuration and being structured and disposed to removably receive a trocar mounted thereon,
- a guide segment extending from said forward end of said insertion arm,
- said guide segment including a pointed tip structured and disposed to facilitate penetration of said guide segment through a patient's skin so as to define a guide port in the patient's skin,
- a penetration resistance hub disposed between said guide segment and said insertion arm, said penetration resistance hub being structured and disposed to abut the patient's skin and thereby resist penetration of said insertion arm through the patient's skin upon initial penetration of said guide segment therethrough, and
- retractable cutting means for cutting at least one incision, extending from said guide port defined in the patient's skin, through the patient's skin, so as to define an entry opening wherethrough said insertion arm and the trocar disposed thereon penetrate the patient's skin, with minimal resistance and minimal skin trauma, to a desired depth.

2. A trocar insertion device as recited in claim 1 wherein said guide segment is substantially narrow in diameter so as to provide facilitated penetration through the patient's skin.

3. A trocar insertion device as recited in claim 1 wherein said guide segment is substantially short so as to minimize a penetration distance thereof through the patient's skin prior to said penetration resistance hub abutting the patient's skin and preventing further insertion thereof.

4. A trocar insertion device as recited in claim 1 wherein said guide segment is generally narrower than said forward end of said insertion arm so as to define said penetration resistance hub therebetween.

5. A trocar insertion device as recited in claim 1 wherein said pointed tip of said guide segment is structured to be removable.

6. A trocar insertion device as recited in claim 5 wherein said guide segment includes a generally hollow, tubular configuration.

7. A trocar insertion device as recited in claim 6 further including viewing means structured and disposed to extend through said guide segment subsequent to removal of said pointed tip therefrom so as to provide an image of a surrounding environment subsequent to insertion of said guide segment through the patient's skin.

8. A trocar insertion device as recited in claim 6 further including insufflation means structured and disposed to extend through said guide segment subsequent to removal of said pointed tip therefrom so as to introduce gas into a patient's abdomen and achieve necessary insufflation thereof subsequent to insertion of said guide segment through the patient's skin.

9. A trocar insertion device as recited in claim 1 wherein said pointed tip of said guide segment is disposed at a distal end of an elongate extension rod structured to extend through a length of said insertion arm such that said pointed tip operatively protrudes from an open end of said guide segment during initial insertion thereof through the patient's skin.

10. A trocar insertion device as recited in claim 9 wherein said pointed tip of said guide segment is independently retractable such that said guide segment remains within said guide port defined thereby, subsequent to the initial penetration through the patient's skin, while said pointed tip is concealed for subsequent insertion of said insertion arm through the patient's skin.

11. A trocar insertion device as recited in claim 10 wherein said pointed tip is structured to remain in a normally concealed orientation unless affirmatively protruded through said open end of said guide segment.

12. A trocar insertion device as recited in claim 1 further including viewing means disposed in said guide segment and structured to provide an image of a surrounding environment subsequent to insertion of said guide segment through the patient's skin.

13. A trocar insertion device as recited in claim 1 further including insufflation means disposed in said guide segment and structured to introduce gas into a patient's abdomen so as to achieve necessary insufflation thereof subsequent to insertion of said guide segment through the patient's skin.

14. A trocar insertion device as recited in claim 1 wherein said retractable cutting means includes at least one surgical blade.

15. A trocar insertion device as recited in claim 14 wherein said surgical blade is tapered outwardly from said guide segment.

16. A trocar insertion device as recited in claim 15 wherein said surgical blade is structured to cut outwardly from said guide port so as to define said entry opening.

17. A trocar insertion device as recited in claim 16 wherein said retractable cutting means includes at least three of said surgical blades, each structured to cut one of said incisions, thereby facilitating minimally traumatic, outward retraction of the patient's skin upon introduction of said insertion arm and the trocar through said entry opening defined by said incisions.

18. A trocar insertion device as recited in claim 17 wherein said surgical blades are secured with one another at a central blade housing so as to facilitate uniform cutting of said incisions thereby.

19. A trocar insertion device as recited in claim 16 wherein said retractable cutting means includes at least four of said surgical blades, each structured to cut one of said incisions, thereby facilitating minimally traumatic, folded retraction of the patient's skin, to fully define said entry opening, upon introduction of said insertion arm and the trocar into said entry opening.

20. A trocar insertion device as recited in claim 19 wherein said surgical blades are secured with one another at a central blade housing so as to facilitate uniform cutting of said incisions thereby.

21. A trocar insertion device as recited in claim 16 wherein said insertion arm includes at least one slit formed at said forward end thereof, said slit being structured and disposed to facilitate retractable protrusion of said surgical blade of said retractable cutting means therethrough from a normally retracted orientation within said insertion arm.

22. A trocar insertion device as recited in claim 21 wherein said slit extends into said guide segment so as to facilitate cutting of said incision from said guide port in the patient's skin.

23. A trocar insertion device as recited in claim 1 further including handle means extending from said rear end of said insertion arm and structured to be grasped by a user and thereby facilitate controlled, selective introduction of said guide segment, said retractable cutting means and said trocar through the patient's skin.

24. A trocar insertion device as recited in claim 1 further including trigger means connected with said retractable cutting means, said trigger means being structured to direct controlled introduction of said retractable cutting means through the patient's skin.

25. A trocar insertion device as recited in claim 24 wherein said trigger means are structured to normally bias and therefore normally maintain said retractable cutting means concealed and shielded in a retracted orientation.

26. A trocar insertion device as recited in claim 25 wherein said trigger means are further structured to automatically retract said retractable cutting means into said retracted orientation immediately upon said retractable cutting means protruding a maximum, safe, cutting distance, thereby ensuring that said retractable cutting means are not over inserted through the patient's skin.

27. A trocar insertion device as recited in claim 1 wherein said retractable cutting means includes an elongate extension segment extending through said insertion arm, towards said rear end thereof, and connected with biasing means structured and disposed to normally urge said elongate extension segment away from said forward end of said insertion arm so as to normally maintain said retractable cutting means concealed and shielded in a retracted orientation.

28. A trocar insertion device as recited in claim 27 further including trigger means connected with said retractable cutting means and structured to gradually and in a controlled fashion direct said retractable cutting means out of said retracted orientation for controlled introduction thereof through the patient's skin.

29. A trocar insertion device as recited in claim 28 wherein said trigger means includes an externally actuatable hammer element structured to engage and push said retractable cutting means out of said retracted orientation into a cutting orientation.

30. A trocar insertion device as recited in claim 29 wherein said hammer element is structured to disengage said retractable cutting means immediately upon said retractable cutting means protruding a maximum, safe, cutting distance, thereby permitting said biasing means to return said retractable cutting means into said retracted orientation and ensuring that said retractable cutting means are not over inserted through the patient's skin.

31. A trocar insertion device comprising:
an insertion arm structured and disposed to removably receive a trocar mounted thereon,
guide means structured to penetrate a patient's skin and define a guide port,
a penetration resistance hub disposed between said guide means and said insertion arm, said penetration resistance hub being structured and disposed to abut the patient's skin and thereby resist penetration of said insertion arm through the patient's skin upon initial penetration of said guide means therethrough, and cutting means for cutting at least one incision, extending from said guide port defined in the patient's skin, through the patient's skin, so as to define an entry opening wherethrough said insertion arm and the trocar disposed thereon penetrate the patient's skin, with minimal resistance and minimal skin trauma, to a desired depth.

32. A trocar insertion device as recited in claim 31 wherein said guide means are substantially narrow in diameter so as to facilitate initial introduction thereof through the patient's skin.

* * * * *